United States Patent
Graetz

Patent Number: 6,144,872
Date of Patent: Nov. 7, 2000

[54] ANALYZING EVENTS IN THE THALAMUS BY NONINVASIVE MEASUREMENTS OF THE CORTEX OF THE BRAIN

[75] Inventor: Galleon Graetz, Meilen, Switzerland

[73] Assignee: Biomagnetic Technologies, Inc., San Diego, Calif.

[21] Appl. No.: 09/302,566

[22] Filed: Apr. 30, 1999

[51] Int. Cl.$^7$ .................................................. A61B 5/05
[52] U.S. Cl. ........................................ 600/409; 600/407
[58] Field of Search .................................. 600/407, 409; 324/244, 248, 252, 260

[56] References Cited

U.S. PATENT DOCUMENTS 4,793,355  12/1988  Crum et al. .
4,977,896  12/1990  Robinson et al. .

(List continued on next page.)

OTHER PUBLICATIONS

Contreras D, Steriade M, State–dependent fluctuations of low–frequency rhythms in corticothalamic networks, in Neuroscience,vol. 76, No. 1, pp. 25–38, 1997.

Jeanmonod D, Magnin M, Morel A, Low threshold calcium spike bursts in the human thalamus, Brain, vol. 119, pp. 363–375, 1996.

Nieuwenhuys R, Voogd J, Van Huijzen C, The human central nervous system, 3rd Edition, pp. 237–246, Springer–Verlag, New York, 1988.

Llinas R, Ribary U, Temporal conjunction in thalamocortical transactions, in Consciousness: at the frontiers of neuroscience, Advances in Neurology, vol. 77, pp. 97–98, Lippincott–Raven Publishers, Philadelphia, 1998.

Llinas R, The intrinsic electrophysiological properties of mammalian neurons: insights into central nervous system function, Science, vol. 242, pp. 1660, 1988.

Makela J, Salmelin R, Kotila M, Salonen O, Laaksenen R, Hokkanen L, Hari R, Modification of neuromagnetic cortical signals by thalamic infarctions, Electroencephalogr and Clinical Neurophysiology, vol. 106, pp. 433–443, 1998

Morel A, Magnin M, Jeanmonod D, Multiarchitectonic and stereotactic atlas of the human thalamus, Journal of Comparative Neurology, vol. 387, pp. 588–630, 1997.

Steriade M, Corticothalamic networks, oscillations and plasticity, in Advances in Neurology, vol. 77, pp. 113–121, Lippincott–Raven Publishers, Philadelphia, 1998.

Steriade M, Gloor P, Llinas R, Lopes DA Silva F, Mesulam M, Basic mechanisms of cerebral rhythmic activities, Electroencephalography and Clinical Neurophysiology, vol. 76, pp. 484–485, 1990.

White E, Termination of thalamic afferents in the cerebral cortex, in Cerebral Cortex, Jones E, Peters A editors, vol. 5, pp. 274–276, Plenum Press, New York, 1986.

Volkmann J, Joliot M, Mogilner A, Ioannides A, Lado F, Fazzini E, Ribary U, Llinas R, Central motor loop oscillations in parkinsonian resting tremor revealed by magnetoencephalography, Neurology, vol. 46, pp. 1359–1370, 1996.

*Primary Examiner*—Teresa Walberg
*Assistant Examiner*—Fadi H. Dahbour
*Attorney, Agent, or Firm*—Gregory Garmong; Eugene Hirschkoff

[57] ABSTRACT

A method for obtaining information about a brain comprises the steps of providing a recording system of the electromagnetic activity produced by the brain, selecting a target pattern of the electromagnetic activity produced by the brain, recording a sample of the electromagnetic activity of the brain using the recording system, and analyzing the sample of the electromagnetic activity of the brain to identify a portion which contains the target pattern. The method further includes identifying a portion which contains the target pattern and which has a focal source at a location in the cortex of the brain, and determining the location in the thalamus which corresponds to the location of this focal source in the cortex of the brain. This determination may be followed by selecting a course of treatment which is directed to the location in the thalamus identified in the step of determining the location in the thalamus, such as a surgical, stimulative, or pharmaceutical treatment.

13 Claims, 3 Drawing Sheets

U.S. PATENT DOCUMENTS

| | | | |
|---|---|---|---|
| 4,996,991 | 3/1991 | Gordon | 600/407 |
| 5,061,680 | 10/1991 | Paulson et al. . | |
| 5,099,864 | 3/1992 | Hardy | 600/407 |
| 5,143,076 | 9/1992 | Hardy et al. | 600/407 |
| 5,200,345 | 4/1993 | Young | 600/407 |
| 5,220,921 | 6/1993 | Ferris et al. | 324/248 |
| 5,437,276 | 8/1995 | Takada | 324/244 |
| 5,444,373 | 8/1995 | Johnson et al. | 324/248 |
| 5,471,985 | 12/1995 | Warden . | |
| 5,494,033 | 2/1996 | Buchanan et al. | 324/248 |
| 5,526,811 | 6/1996 | Lypchuk . | |
| 5,713,354 | 2/1998 | Warden | 600/409 |
| 5,748,767 | 5/1998 | Raab | 600/407 |

ANALYZING EVENTS IN THE THALAMUS BY NONINVASIVE MEASUREMENTS OF THE CORTEX OF THE BRAIN

BACKGROUND OF THE INVENTION

This invention relates to the analysis of the functioning of the brain, and, more particularly, to the analysis of the functioning of the thalamus by measurements made on the cortex of the brain.

Many of the most baffling disorders of the human body are associated with disorders of the brain. Examples include epilepsy, schizophrenia, Parkinson's disease, and chronic depression. Such disorders are difficult to analyze, understand, and treat, in part because it is not clear in some cases whether they are physical or non-physical in origin, or involve a complex interweaving of physical and non-physical causes. One of the great challenges in modern medicine is to analyze the nature and origin of these disorders, understand the mechanism of the disorders, and then treat the disorders.

In some cases, the disorders appear to involve malfunctions in a portion of the brain of a person, the manifestation of which is a so-called positive symptom. Typical positive symptoms include tremor, pain, or seizure. In some of these cases, it has been possible to alleviate the positive symptom by disrupting the communications paths between the different parts of the brain. This disruption thus provides a significant improvement in the quality of life for that person.

The thalamus is a portion of the brain which is central to the communication between the cortex, where higher sensory, motor, and cognitive functions are located, and the remainder of the body. Therefore, it has been a focus of attention for the development of therapies which address various disorders and various positive symptoms. Different physical locations in the thalamus where these abnormal rhythms occur appear to be associated with different disorders or positive symptoms. For example, it has been observed that certain positive symptoms appear to be characterized by the occurrence of characteristic patterns of electrical activity (such as abnormal low-frequency rhythmic electrical voltages) in certain groups of cells within the thalamus, and that the destruction of these cells through a surgical procedure such as a thalamotomy produces a marked reduction of the positive symptoms. Another example of therapy targeted at the thalamus is the use of electrical stimulators implanted within the thalamus of persons suffering from Parkinson's tremor. When properly placed, activation of the stimulator has been observed to arrest the tremor.

The association of brain disorders with specific locations in the thalamus has been determined largely by invasive studies using electrical probes inserted into the brain of a patient undergoing brain surgery. No techniques are available for determining these locations non-invasively and prior to surgery. Methods such as positron emission tomography (PET) or functional magnetic resonance imaging (fMRI) detect secondary effects of the disorder such as oxygen concentration or metabolism rather than the primary functional activity of the disorder itself. Current electroencephalography (EEG) procedures, while detecting basic functional activity of the disorder, lack the capability to associate the measured voltages to the precise physical locations of the sources of those voltages within the brain to resolutions of a few millimeters, because of the electrical resistivity of the tissue making up the brain, skull, and scalp. Magnetoencephalography (MEG) also detects the basic functional activity of the disorder and also has the ability to determine the locations within the brain more accurately than EEG owing to the transparency of the tissues making up the head to magnetic fields. However, the rapid decay of the magnitude of magnetic signals with distance from the source (typically falling off as the inverse square of the distance) limits the practical sensitivity of that technique primarily to cortical sources. (Electrical signals also rapidly decay with distance, so EEG suffers from this same limitation.) The thalamus is located in the central region of the brain, and therefore sources in the thalamus are not readily measurable by MEG or EEG.

A non-invasive approach for observing and providing information about abnormal electrical activity occurring in the central region of the brain to within a fine spatial resolution would enable physicians to determine whether a patient suffering from a particular brain disorder might be a candidate for therapy aimed at that central region without an invasive procedure for the purposes of the determination. If the patient were such a candidate, this approach could also provide information as to where to target an appropriate therapy and which therapeutic approach is optimal.

Thus, there is needed a technique for noninvasively measuring and analyzing dysfunctional activity associated with specific locations of the thalamus or other portions of the central region of the brain. Once such a technique is available, there would be an associated opportunity for treating the disorder. The present invention fulfills these needs, and further provides related advantages.

SUMMARY OF THE INVENTION

This invention relates to a technique for obtaining information about the brain and using that information to analyze disorders within the brain. In particular, this technique allows information to be inferred about dysfunctions occurring at specific locations deep within the brain, for example in the thalamus. The technique is noninvasive and operable in vivo. Its results may be used as a direct basis for the diagnosis and/or selection of a treatment for the disorder and for guiding and monitoring the application of the treatment.

In accordance with the invention, a method for obtaining information about a brain comprises the steps of providing a recording system of the electromagnetic activity produced by the brain, selecting a target pattern of the electromagnetic activity produced by the brain, and recording a sample of the electromagnetic activity of the brain using the recording system. The method further includes analyzing the sample of the electromagnetic activity of the brain to identify a portion which contains the target pattern, identifying a portion which contains the target pattern and which also has a focal source at a location in the cortex of the brain, and determining the location in the thalamus which corresponds to the location of the focal source in the cortex of the brain. This process may be followed by selecting a course of treatment which is directed to the location in the thalamus identified in the step of determining the location in the thalamus, such as surgical intervention in the thalamus, stimulating the thalamus using an implanted stimulator, or administering a pharmaceutical which acts upon the determined location of the thalamus.

The recording system is preferably a biomagnetometer. The biomagnetometer, using sensitive detectors positioned outside the head, noninvasively measures the magnetic fields associated with electrical activity originating at specific locations within the brain. However, because the magnitude of the magnetic fields is small, and because the magnitude falls rapidly with increasing distance from their source, the biomagnetometer most effectively measures the magnetic fields originating in the near-surface regions of the brain. That is, the biomagnetometer is most effectively used for measuring and identifying the location of sources located only in the cortex of the brain. While the biomagnetometer may be able to detect a signal coming from deeper locations in the brain, the spatial resolution in determining the location of such a deeper source is diminished because of the decrease in the signal-to-noise ratio for such a signal.

The present approach provides for identifying and determining the location of certain electrical activity occurring at specific locations within the deep brain, notably the thalamus, by identifying and locating correspondent electrical activity occurring at specific locations within the cortex. In particular, abnormal patterns of deduced activity occurring within the thalamus and associated with a specific disorder are sometimes associated with the correspondent patterns of activity occurring at one or more locations within the cortex. By making measurements of the magnetic fields produced by cortical electrical activity using the biomagnetometer or other approach, the existence of a pattern of electrical activity that is characteristic of the specific disorder may be detected. If so detected, the location of the source or sources of that cortical activity is determined. Upon the determination of the location of such source or sources, the location of the associated thalamic activity is deduced, from preexisting information about the corticothalmic or other interconnecting pathways.

Identifying the exact location in the thalamus related to a disorder is important beyond gaining an understanding of that disorder, because that information may be used in selecting and applying a course of treatment. It may be possible to surgically intervene in some cases or apply other physically localized treatments such as an implanted stimulator. In other cases, surgery may be inappropriate or ineffective if directed to this location in the thalamus, and pharmaceutical or other treatments may be preferable in view of the patient's physical condition.

The present approach determines the location of the source of electrical activity in the thalamus which is associated with the disorder, and then guides the selection and application of the treatment. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
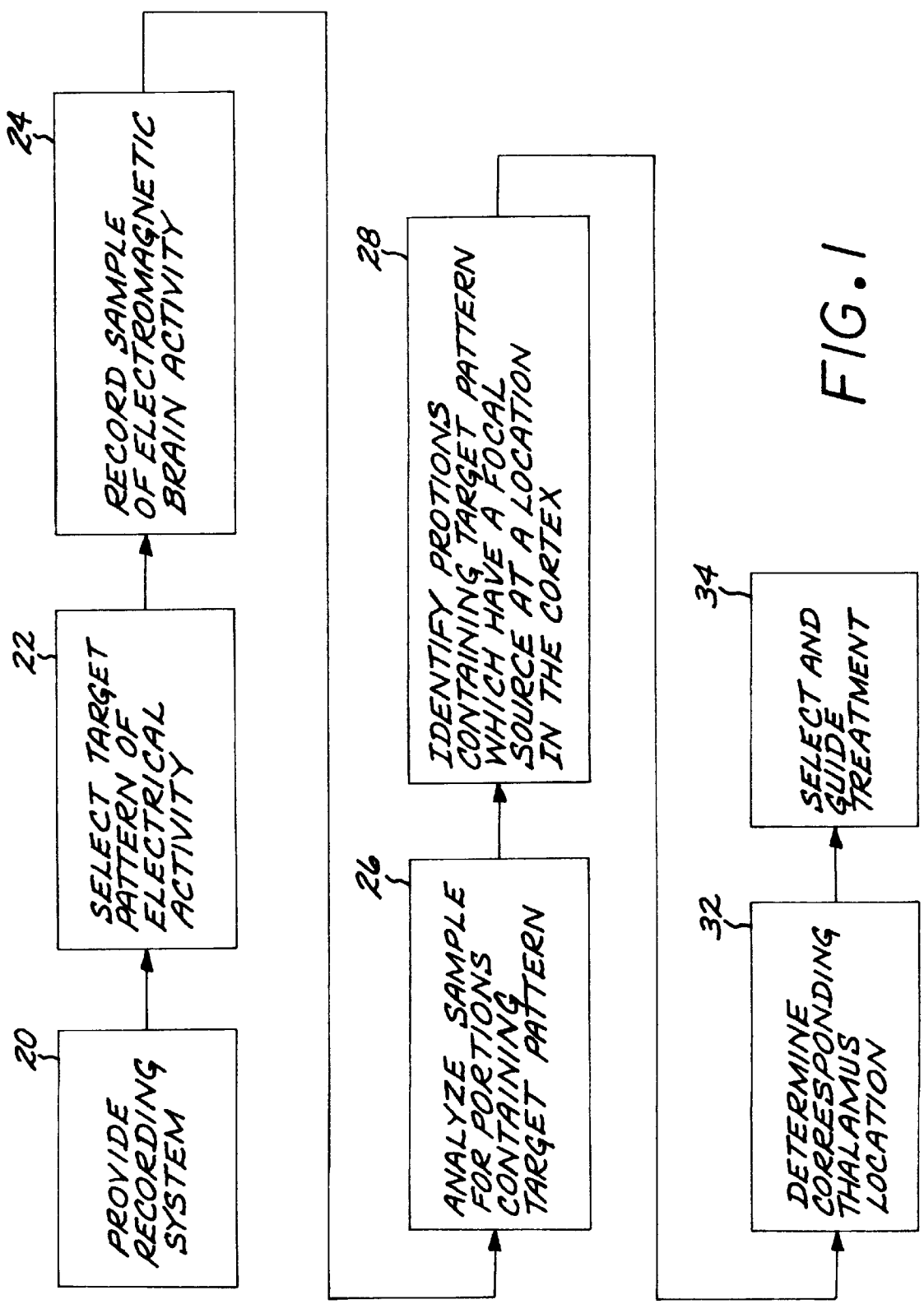
FIG. 1 is a block flow diagram of an approach for practicing the present invention.
Figure 2:
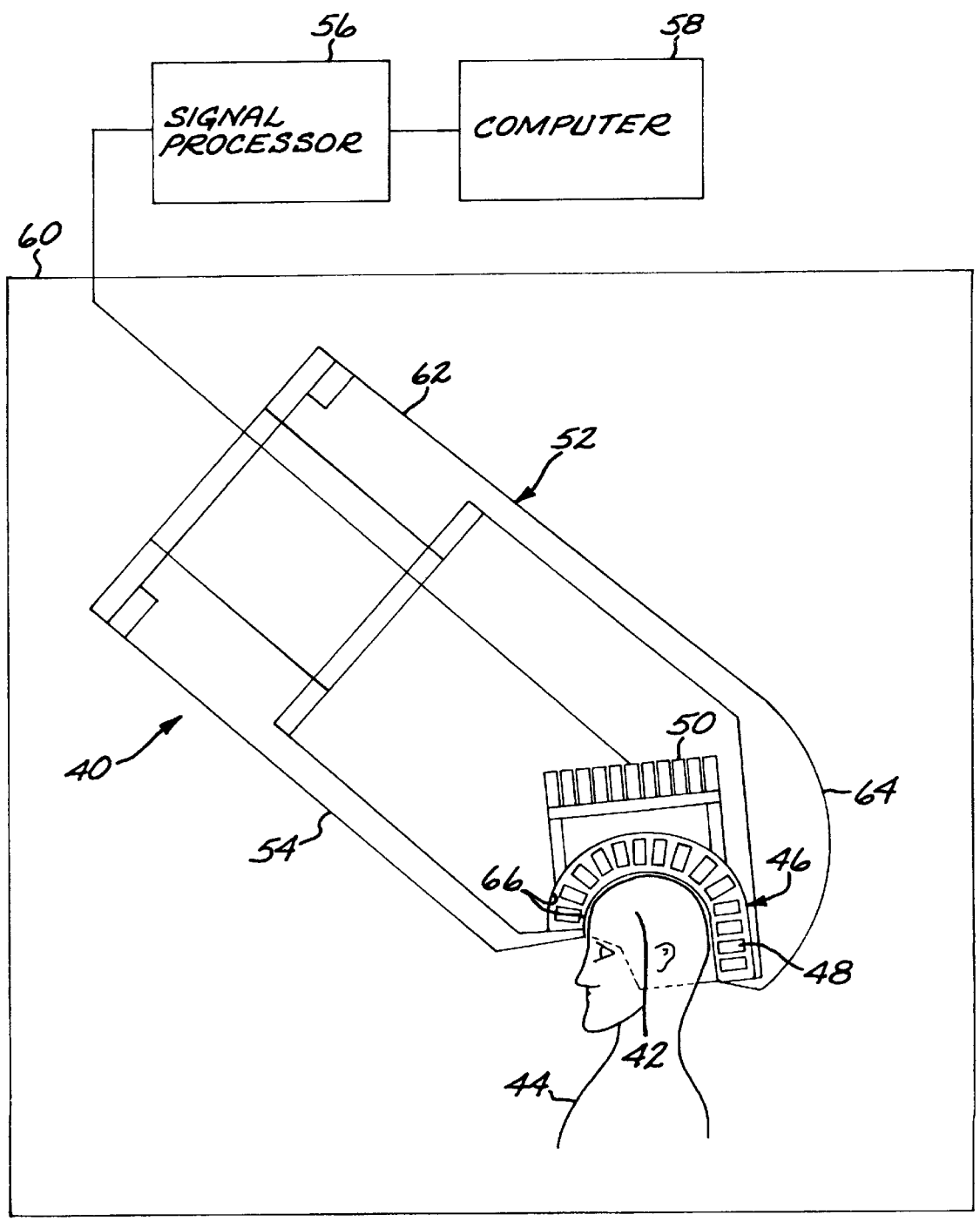
FIG. 2 is a schematic diagram of a biomagnetometer.

FIG. 1 depicts a preferred procedure for practicing the invention. A recording system is provided, numeral 20. FIG. 2 illustrates a preferred form of the recording system, a biomagnetometer apparatus 40 for obtaining biomagnetic data from a brain 42 located within a head of a human subject 44. The biomagnetometer apparatus 40 includes an array 46 of magnetic field sensors in the form of magnetic field pickup coils 48 for measuring small magnetic fields. The pickup coils 48 may be magnetometers or gradiometers, or of other configuration as may be appropriate for a particular application.

The output signal of each magnetic field pickup coil 48 is detected by a detector, preferably a superconducting quantum interference device 50 ("SQUID"). There is typically one SQUID 50 for each pickup coil 48. These components, together with the associated electronics, form a single channel. A typical apparatus 40 may have tens or hundreds of channels that simultaneously detect the magnetic fields at various locations around the head of the subject 44.

Both the magnetic field pickup coil 48 and the SQUID 50 are maintained at a cryogenic operating temperature within a vacuum-insulated dewar vessel 52 that has a vacuum-supporting wall and appropriate insulation. An outer wall 54 of the dewar vessel 52 functions as its external body. The dewar vessel 52 functions as an insulated container that contains a cryogenic liquid therein. The required type of cryogenic liquid is determined in part by the cooling requirements of the SQUID. In most instances, measurements of signals produced by the brain require a low temperature to suppress temperature-dependent noise and to operate the most-sensitive detectors, and liquid helium is used as the cryogenic liquid. The present invention is also operable in conjunction with advanced dewar designs in which the pickup coils and/or SQUIDs are supported in a vacuum rather than immersed in the cryogenic liquid.

The electronics arrangement of the biomagnetometer apparatus 40 is illustrated schematically in FIG. 2. The magnetic signals from the brain are sensed by the magnetic field pickup coil 48, which produces a small electrical current output signal when penetrated by magnetic flux. The output signal of the pickup coil 48 is detected by the detector, in this case the SQUID 50. The SQUID 50 produces an electrical voltage proportional to the magnetic flux detected by the pickup coil. The output signal of the SQUID 50 is processed in an ambient-temperature electronic signal processor 56, which typically includes balancing, gain, amplifying, noise reduction, and filtering circuitry, and stored and analyzed in a computer 58 as a function of time. Each sensor channel results in a record of its response to the magnetic field produced by all of the sources within the subject brain, as those sources act simultaneously on the pickup coil of the sensor channel. For clarity, FIG. 2 depicts only a single sensor channel including a pickup coil and a SQUID, but in practice there is typically a signal processor 56 for each of the SQUID 50/pickup coil 48 sets.

The biomagnetometer apparatus 40 and the subject 44 are preferably, but not necessarily, enclosed within a magnetically shielded room 60, also termed an MSR, that shields the apparatus 40 from external influences. By screening off the external influences, the amount of signal processing and filtering required to obtain a meaningful indication of the biomagnetic field are reduced. The signal processor 56 and computer 58 are typically located outside the MSR 60, so that they do not interfere with the sensing of the magnetic field of the subject 44.

As shown in FIG. 2, the pickup coils 48 are desirably arranged in the helmet-shaped array 46 that is contained within the wall 54. In the preferred embodiment, an upper portion 62 of the wall 54 is cylindrical. A lower portion 64 of the wall 54 is shaped to include a helmet-shaped recess 66 that is sized to receive the head 22 of the subject 24 therein. It is desirable that the pickup coils 48 be located as close as possible to the magnetic field sources within the brain 42 of the subject 44. The helmet-shaped recess 66 in the wall 54 is therefore cooperatively structured with the array 46 of pickup coils 48, so that the individual pickup coils 48 are positioned closely adjacent to the interior wall of the helmet-shaped recess 66. The surface of the recess 66 is substantially in the shape of a headform cranial portion of a human headform.

The basic structure of the components of this system are known. The construction of vacuum enclosures is disclosed in U.S. Pat. No. 4,773,952. The construction and operation of magnetic field sensors, including pickup coils, SQUIDs, and ambient-temperature SQUID electronics are disclosed in U.S. Pat. Nos. 3,980,076; 4,079,730; 4,386,361; and 4,403,189. A biomagnetometer is disclosed in U.S. Pat. No. 4,793,355. Magnetically shielded rooms are disclosed in U.S. Pat. Nos. 3,557,777 and 5,043,529. The disclosures of all of these patents are incorporated herein by reference.

In some instances, the recording system may be an electroencephalograph rather than a biomagnetometer. The electroencephalograph makes measurements of the electrical signals produced by the brain, and from these measurements the locations of the sources in the brain are deduced. Electroencephalography (EEG) is less preferred than magnetoencephalography (MEG) for use in the present invention, because of its lesser ability to identify the locations of the sources of the measured signals with high spatial resolution. It is strongly preferred that the recording system be capable of locating cortical sources to within a resolution of at least about 4 millimeters, because there is substantially less confidence in associating cortical sources with thalamic sources if the resolution limit of the measurement adds a larger uncertainly to the result.

Returning to FIG. 1, for the purposes of analyzing the output of the detectors SQUIDs 50 as processed by the signal processor 56 and stored within the computer 58, a target pattern of electrical activity of interest is selected, numeral 22. The preferred target pattern of electrical activity for analyzing cortical-thalamic relations pertinent to a number of brain disorders has been determined to be activity for which the frequency spectrum contains components in a relatively low-frequency range, from about 1 Hertz to about 40 Hertz, preferably from about 2 Hertz to about 10 Hertz. This selection is made because rhythmic activity in this range has been observed in patients with the brain disorders of interest during the course of surgical procedures.

Figure 3:
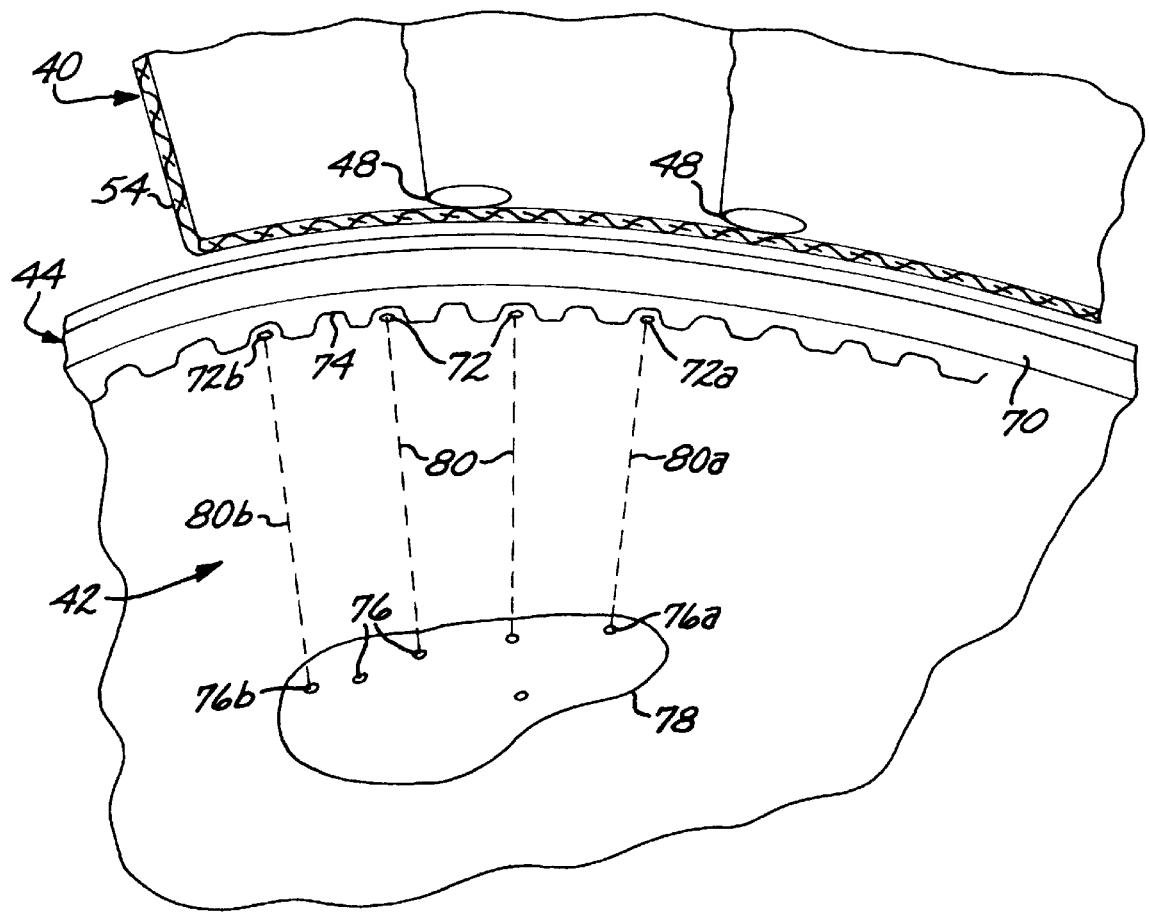
FIG. 3 is a schematic detail of the biomagnetometer located adjacent to the head of the subject.

FIG. 3 depicts the relationship of the pickup coils 48 of the biomagnetometer 40 to the brain 42 of the subject 44 in greater detail. The magnetic fields produced by the brain 42 of the subject 44 are quite small, on the order of $10^{-14}$ Tesla. The magnitude of these magnetic fields decays rapidly with increasing distance from the source to even smaller levels. The pickup coils 48 are separated from the brain 42 by the thickness of the human skull 70 and the thickness of the outer wall 54 and thermal insulation of the dewar vessel 52. Within the level of instrumentation available now, and expected to be available for the foreseeable future, the pickup coils 48 provide the location of the electrical activity with a spatial resolution of about 4 millimeters for signals coming from sources in cortical locations 72 in the outer regions of the cortex 74 of the brain 42. Magnetic fields produced by thalamic sources at thalamus locations 76 of the thalamus 78, which is buried deeper within the brain 42 and therefore substantially further from the pickup coils 48 than the cortical locations 72, can be detected only weakly, if at all. The spatial resolution that is available when thalamic sources are detected is much poorer than 4 millimeters and is generally too poor to be useful to the physician. The biomagnetometer 40 therefore cannot directly determine the locations of sources within the thalamus to the required resolution for study and therapy.

However, there is evidence to indicate that cortex sources located at cortex locations 72 function in relation to respective thalamus sources located at thalamus locations 76. The functional relations are indicated schematically by a link 80, but the electrical and chemical nature of the link is not known with certainty. For example, and as illustrated in FIG. 3, a first cortex source located at a first cortex location 72a functions through a link 80a in relation to a respective first thalamus source located at a first thalamus location 76a; a second cortex source located at a second cortex location 72b functions through a link 80b in relation to a respective second thalamus source located at a second thalamus location 76b; and so on. The exact mechanism of these relationships and the links is not known in all cases at this time.

Knowledge of these mechanisms is not necessary for the operation of the present invention, and it is expected that the utilization of the present invention will aid in research in understanding these links and mechanisms. For the present invention, it is necessary only that there exist functional interrelationships between cortex sources and thalamus sources that have observable consequences. It is also significant that the relationships between specific cortex sources at specific cortex locations may be associated with specific thalamus sources at specific thalamus locations. Such specific relationships may be represented as a mapping, schematically as individual links 80a, 80b, etc. in FIG. 3.

There are thalamus sources 76 which exhibit oscillatory or rhythmic electrical activity, when the brain is affected by a disorder of interest, in the target frequency range of from about 1 Hertz to about 40 Hertz, and specifically are most active in the target frequency range of from about 2 Hertz to about 10 Hertz. This oscillatory activity is evidenced in corresponding oscillatory activity in the cortex sources at the cortex locations 72.

As depicted in FIG. 1, a sample of electromagnetic activity produced by the brain 42 of the subject 44 is recorded by the biomagnetometer 40, with the data stored in the computer 58, numeral 24. In a currently available biomagnetometer 40, this data includes as many as 148 channels of data taken from that number of pickup coils 48 spaced around the brain 42 of the subject 44. As noted above, the biomagnetometer 40 reliably obtains information from the cortex sources located at the cortex locations 72, but not directly from any electromagnetic activity at the thalamus locations 76.

The raw sample data typically includes all patterns of electrical activity that are measurable by the biomagnetometer 40, not just the target patterns of interest. The sample is analyzed to identify a portion which contains the target pattern, numeral 26. In the preferred case, the raw sample data that contain the target frequency components of interest (e.g., frequency components in the 1–40 Hertz range) are identified using well known techniques such as Fourier analysis or filtering.

The sample portion containing the target pattern and which has a focal source at the cortex location 72 in the cortex of the brain is identified, numeral 28. That is, some or all of the sample portions containing the target pattern, as isolated in step 26, may originate in one or more sources located within the cortex. The location of any such source in the cortex is identified in step 28. This identification may be performed by any operable technique known in the art, such as the single equivalent current dipole model or the spatial filter technique described in U.S. Pat. Nos. 4,977,896 and 5,269,325. The data containing the frequency components in the target frequency range is scanned on a millisecond-by-millisecond basis to determine whether the measured magnetic field pattern is well described by the single equivalent dipole model or the spatial filter model. The location 72 of the source in the cortex is determined according to the appropriate single equivalent current dipole model or the spatial filter technique. In a typical case, there may be multiple sources identified at multiple locations within the cortex.

The thalamus location 76 of the thalamus source which corresponds to the cortex location 72 of the cortex source determined in step 28 is identified and determined, numeral 32. This step is performed by applying a cortico-thalamic map such as that depicted schematically in FIG. 3 for the linked sets such as 72*a*-80*a*-76*a*. At the present time, the preferred such cortico-thalamic map is that set forth in R. Nieuwenhuys et al., *The Human Central Nervous System*, (1988), published by Springer Verlag, see particularly page 244 and FIGS. 167 and 217A–B. Other mappings may be used as appropriate, particularly as the understanding of cortico-thalamic relationships improves and the mappings are refined.

The information regarding thalamus locations 76 of the thalamus sources may be used directly for studies of the relationships and links between the thalamus sources and the cortex sources at the cortex locations 72.

The information may also be used to select and guide a course of treatment, numeral 34. Such a treatment may include any operable type for the condition being treated and may include, for example, surgical intervention, surgically implanting a therapeutic device such as an implanted stimulator, or selective pharmaceuticals which act on specific regions of the thalamus. Because the precise location of the thalamus source is known using the approach of steps 20, 22, 24, 26, 28, and 32, the treatment may be made highly specific to the thalamus location 76 associated with a specific disorder.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for obtaining information about a brain, comprising the steps of:

providing a recording system of the electromagnetic activity produced by the brain;

selecting a target pattern of the electromagnetic activity produced by the brain;

recording a sample of the electromagnetic activity of the brain using the recording system;

analyzing the sample of the electromagnetic activity of the brain to identify a portion which contains the target pattern;

identifying a portion of the sample which contains the target pattern and which also has a focal source at a location in the cortex of the brain; and determining the location in the thalamus which corresponds to the location of the focal source in the cortex of the brain.

2. The method of claim 1, wherein the step of providing a recording system includes the step of providing a biomagnetometer system.

3. The method of claim 1, wherein the step of providing a recording system includes the step of providing a recording system having a spatial resolution of no more than about 4 millimeters for sources in the cortex of the brain.

4. The method of claim 1, wherein the step of providing a recording system includes the step of providing an electroencephalography system.

5. The method of claim 1, wherein the step of selecting a target pattern includes the step of selecting a target frequency range of from about 1 Hertz to about 40 Hertz.

6. The method of claim 1, wherein the step of selecting a target pattern includes the step of selecting a target frequency range of from about 2 Hertz to about 10 Hertz.

7. The method of claim 1, wherein the step of identifying includes the step of applying a single equivalent current dipole model.

8. The method of claim 1, wherein the step of identifying includes the step of applying a spatial filter.

9. The method of claim 1, wherein the step of determining the location in the thalamus includes the step of applying a cortico-thalamic map.

10. The method of claim 1, including an additional step, after the step of determining the location in the thalamus, of selecting a course of treatment which is directed to the location in the thalamus identified in the step of determining the location in the thalamus.

11. The method of claim 10, wherein the step of selecting a course of treatment includes the step of selecting a surgical intervention in the thalamus.

12. The method of claim 10, wherein the step of selecting a course of treatment includes the step of stimulating the thalamus using an implanted stimulator.

13. The method of claim 10, wherein the step of selecting a course of treatment includes the step of administering a pharmaceutical which acts upon the determined location in the thalamus.

* * * * *